(12) United States Patent
Ramesh et al.

(10) Patent No.: US 11,412,957 B2
(45) Date of Patent: Aug. 16, 2022

(54) NON-CONTACT IDENTIFICATION OF GAIT DYNAMICS, PATTERNS AND ABNORMALITIES FOR ELDERLY CARE

(71) Applicant: Tellus You Care, Inc., San Francisco, CA (US)

(72) Inventors: Srivatsan Ramesh, San Francisco, CA (US); Kevin Hsu, San Francisco, CA (US); Tania Abedian Coke, San Francisco, CA (US)

(73) Assignee: Tellus You Care, Inc., San Francisco, CA (US)

( * ) Notice: Subject to any disclaimer, the term of this patent is extended or adjusted under 35 U.S.C. 154(b) by 329 days.

(21) Appl. No.: 16/886,887

(22) Filed: May 29, 2020

(65) Prior Publication Data

US 2020/0383608 A1 Dec. 10, 2020

Related U.S. Application Data

(60) Provisional application No. 62/858,406, filed on Jun. 7, 2019.

(51) Int. Cl.
| | |
|---|---|
| *A61B 5/11* | (2006.01) |
| *G01S 13/66* | (2006.01) |
| *A61B 5/00* | (2006.01) |
| *G06N 20/00* | (2019.01) |

(52) U.S. Cl.
CPC ............ *A61B 5/112* (2013.01); *A61B 5/1115* (2013.01); *A61B 5/1118* (2013.01); *A61B 5/1122* (2013.01); *A61B 5/746* (2013.01); *G01S 13/66* (2013.01); *A61B 2503/08* (2013.01); *G06N 20/00* (2019.01)

(58) Field of Classification Search
CPC ..... A61B 5/112; A61B 5/1115; A61B 5/1118; A61B 5/1122; A61B 5/746; A61B 2503/08; A61B 5/0507; A61B 5/1126; G01S 13/66; G01S 7/415; G01S 7/417; G01S 7/4802; G01S 13/726; G01S 13/865; G01S 13/867; G01S 17/89; G01S 13/0209; G06N 20/00
USPC .......................................................... 600/595
See application file for complete search history.

(56) References Cited

U.S. PATENT DOCUMENTS

| | | | |
|---|---|---|---|
| 9,408,561 B2 * | 8/2016 | Stone ..................... | A61B 5/112 |
| 2016/0073614 A1 * | 3/2016 | Lampe .................. | A61B 5/7267 |
| | | | 600/595 |
| 2017/0243354 A1 * | 8/2017 | Tafazzoli ............. | A61B 5/7275 |

* cited by examiner

*Primary Examiner* — Omar Casillashernandez

(74) *Attorney, Agent, or Firm* — Muirhead and Saturnelli, LLC

(57) ABSTRACT

Determining gait patterns and abnormalities of a user includes forming a plurality of point clouds corresponding to the user, each of the point clouds being three-dimensional coordinates of moving points, frame by frame, through a data capturing session, determining centroids of the point clouds, determining momentary walking velocities using estimates based on vectors connecting the centroids for adjacent frames captured during walking of the user, determining gait speed for the user based on the momentary walking velocities, determining at least one distribution of gait speeds for the user, and detecting gait abnormalities based on deviation of the gait speed from the at least one distribution of gait speeds. Detecting a plurality of point clouds may include using a tracking device to capture movements of the user. The tracking device may use radar and/or lidar. The system may determine a gait pattern of the user corresponding to routines of the user.

16 Claims, 5 Drawing Sheets

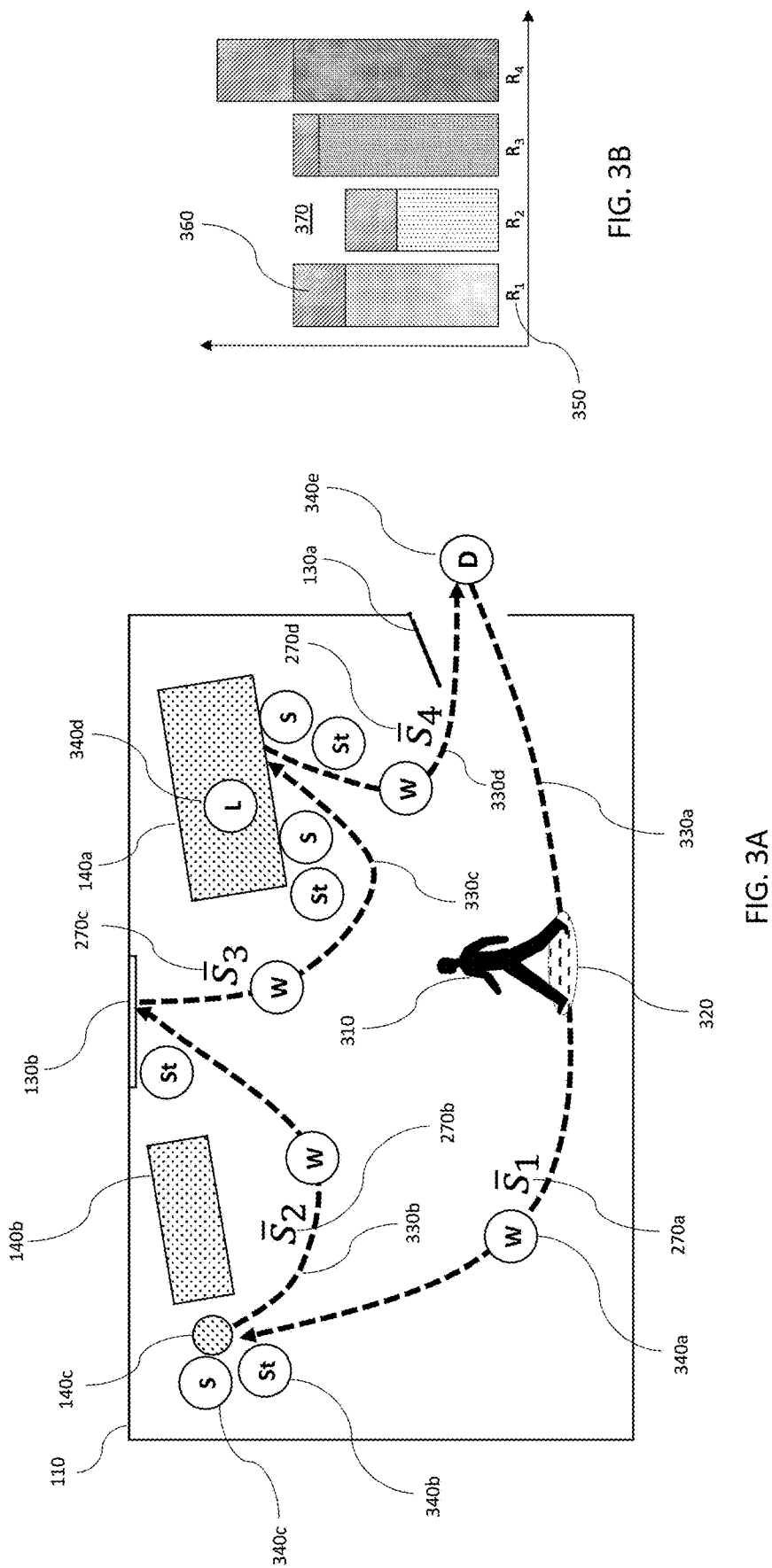

NON-CONTACT IDENTIFICATION OF GAIT DYNAMICS, PATTERNS AND ABNORMALITIES FOR ELDERLY CARE

CROSS-REFERENCE TO RELATED APPLICATIONS

This application claims priority to U.S. Prov. App. No. 62/858,406, filed on Jun. 7, 2019, and entitled "NON-CONTACT IDENTIFICATION OF GAIT DYNAMICS, PATTERNS AND ABNORMALITIES FOR ELDERLY CARE", which is incorporated herein by reference.

TECHNICAL FIELD

This application is directed to the field of remote monitoring of walking parameters and patterns using interconnected hardware and software, and machine learning, and more particularly to remote identification of gait dynamics, patterns and detecting gait abnormalities with elderly people using an ultra-wideband radar and machine learning.

BACKGROUND OF THE INVENTION

Rhythmic, balanced and sufficiently fast gait is an important factor of human wellness. Gait quality and speed often deteriorates with age and gait abnormalities represent a challenge for many seniors. Thus, according to one study, in a sample of noninstitutionalized older adults, 35 percent were found to have an abnormal gait. In another study, gait disorders were detected in approximately 25 percent of persons 70 to 74 years of age, and nearly 60 percent of those 80 to 84 years of age.

Many researchers agree that determining gait abnormalities can be challenging, because there are no clearly accepted standards to define a normal gait in an older adult. Studies comparing healthy persons in their 70s with healthy persons in their 20s demonstrate a 10 to 20 percent reduction in gait speed and stride length in the older population. Other characteristics of gait that commonly change with aging include an increased stance width, increased time spent in the double support phase (i.e., with both feet on the ground), bent posture, and less vigorous force development at the moment of push off.

Some elements of gait typically change with aging, while others do not. A key gait characteristic is the gait velocity (speed of walking), which normally remains stable until about age 70; subsequently, gait speed tends to decline on average about 15% per decade for usual walking and 20% per decade for fast walking. Numerous studies prove that gait speed of a senior person is a powerful predictor of mortality—in fact, gait speed is as powerful an indicator as an elderly person's number of chronic medical conditions and hospitalizations. According to health statistics, at age 75, slow walkers die on average over 6 years earlier than normal velocity walkers and more that 10 years earlier than fast velocity walkers.

From the standpoint of body mechanics, gait speed typically declines with age because elderly people take shorter steps at the same rate. A number of health conditions may contribute to dysfunctional or unsafe gait: the list includes neurologic disorders, such as dementias; movement and cerebellar disorders; sensory or motor neuropathies; and musculoskeletal disorders, for example, spinal stenosis. Gait disorders may manifest itself in many different ways, such as the loss of symmetry of motion, difficulty initiating or maintaining a rhythmic gait, walking backwards when initiating gait, falling backwards while walking, deviations from walking path and many more defects.

Traditionally, gait disorders have been diagnosed and analyzed through a multi-phase process that included collecting patient's complaints, observing gait with and without an assistive device, assessing all components of gait dynamics, and observing patient's gait repetitively with a knowledge of the patient's gait components and deviations. With aging world population and increased percentage of seniors residing in long-term elderly care facilities, the healthcare industry is developing technologies and applications for continuous contact and non-contact monitoring of seniors at an accelerated pace. Examples include gait analysis systems based on motion capture devices (Microsoft Kinect and similar), an experimental WiGait RF device by MIT researchers, etc.

Notwithstanding some progress in developing non-contact continuous gait monitoring devices and systems, there are many unsolved problems in the area of automated gait analysis.

Many practitioners are still using outdated gait speed measurement techniques, such as a 10-meter walking test timed by a stopwatch, whereas more advanced wearable and laboratory solutions, such as RunScribe ShoeRide, Stryd or ProKinetics's Zeno Walkway don't allow permanent gait measurements in real-life environments with complex and diversified user behaviors and routines. Camera-based motion capturing technologies often conflicts with privacy requirements by seniors, while an experimental WiGait device captures a single body point per frame, which is insufficient for retrieving gait patterns and detecting gait abnormalities.

Accordingly, it is desirable to develop new techniques and systems for reliable gait monitoring, identification of gait patterns and detection of gait abnormalities.

SUMMARY OF THE INVENTION

According to the system described herein, determining gait patterns and abnormalities of a user includes forming a plurality of point clouds corresponding to the user, each of the point clouds being three-dimensional coordinates of moving points, frame by frame, through a data capturing session, determining centroids of the point clouds, determining momentary walking velocities using estimates based on vectors connecting the centroids for adjacent frames captured during walking of the user, determining gait speed for the user based on the momentary walking velocities, determining at least one distribution of gait speeds for the user, and detecting gait abnormalities based on deviation of the gait speed from the at least one distribution of gait speeds. Detecting a plurality of point clouds may include using a tracking device to capture movements of the user. The tracking device may use radar and/or lidar. The movements may be associated with states corresponding to walking, standing, sitting, lying down on a bed, lying down on a floor, and/or departing a room. Determining gait patterns and abnormalities of a user may also include determining a gait pattern of the user corresponding to routines of the user based on routes walked by the user, where a separate one of the at least one distribution of gait speeds is provided for each of the routines. Determining gait patterns and abnormalities of a user may also include providing an alarm in response to detecting gait speeds for a subset of the routines that deviate from the gait pattern. The alarm may be provided with identification of specific ones of the routines for which the gait speed of the user deviates. The routes may correspond to the movements of the user between objects in a room.

According further to the system described herein, a non-transitory computer readable medium contains software that determines gait patterns and abnormalities of a user. The software includes executable code that forms a plurality of point clouds corresponding to the user, each of the point clouds being three-dimensional coordinates of moving points, frame by frame, through a data capturing session, executable code that determines centroids of the point clouds, executable code that determines momentary walking velocities using estimates based on vectors connecting the centroids for adjacent frames captured during walking of the user, executable code that determines gait speed for the user based on the momentary walking velocities, executable code that determines at least one distribution of gait speeds for the user, and executable code that detects gait abnormalities based on deviation of the gait speed from the at least one distribution of gait speeds. Detecting a plurality of point clouds may include using a tracking device to capture movements of the user. The tracking device may use radar and/or lidar. The movements may be associated with states corresponding to walking, standing, sitting, lying down on a bed, lying down on a floor, and/or departing a room. The software may also include executable code that determines a gait pattern of the user corresponding to routines of the user based on routes walked by the user, where a separate one of the at least one distribution of gait speeds is provided for each of the routines. The software may also include executable code that provides an alarm in response to detecting gait speeds for a subset of the routines that deviate from the gait pattern. The alarm may be provided with identification of specific ones of the routines for which the gait speed of the user deviates. The routes may correspond to the movements of the user between objects in a room.

The proposed system offers continuous non-contact user monitoring with identification of walking direction and gait speed. The system may accumulate gait statistics and patterns associated with everyday user routines, compare the gait statistics and patterns with newly captured data, detect gait abnormalities and generate reports and instant warnings for user conditions where gait parameters noticeably deviate from the regular patterns.

Various aspects of system functioning are explained as follows.
1. A tracking device constantly captures high precision data from moving objects in a room where a user resides. Movements may include walking, standing, sitting, and lying down on a bed or a floor; movements with a smaller amplitude may indicate breathing and heartbeat. The device may include one or multiple radars, as well as lidars or other non-camera-based motion capturing technologies. In some cases, using cameras may be considered detrimental to user privacy, especially during round-the-clock monitoring, such as in long-term elderly care facilities, inpatient hospital care, etc.
2. Captured data may be presented in the form of point clouds, showing three-dimensional coordinates of moving points, frame by frame, through a data capturing session. Frame frequency may be determined by technical characteristics of tracking devices, by computing, storage and data transmission environment, by data accuracy requirements, etc. For many tasks, frame frequency of four frames per second may be considered satisfactory.
3. Point clouds associated with subsequent frames may be pre-processed in several steps:
    a. Cleaning up point clouds, which includes filtering out redundant points.
    b. Calculating positions of centroids of point clouds.
    c. Determining momentary walking velocities, speed and walking direction using estimates based on a sequence of centroids for adjacent frames and on vectors connecting such adjacent centroids of point clouds for neighboring frames captured during user walk.
4. Further insights into geometry and dynamics of frame-by-frame point clouds may allow estimates of other important gait parameters, such as step count, step length and symmetry or asymmetry of steps within a stride. Point clouds for a walking user, captured by a non-contact device at different phases of a step or a stride, may have different geometry and distribution of velocities in the lower portion of the user body, following the movements of a reference foot. Specifically, the width of the lower body may oscillate between a narrow column, corresponding to a mid-swing part of a step when the trajectory of the swinging foot crosses the relatively static position of the other foot, to a wide triangle formed by two legs separated by a maximum distance at the heel strike end of a step. Accordingly, point velocity increases on the side of the swinging foot from the toe off position until the mid-swing and then decreases all the way until the next heel strike phase. Systematically collecting and processing point coordinates and velocities may allow estimating step count and length, walking base, gait symmetry, duration of single and double support phases, etc.
5. The system may compile a list of user routines (activities) that may include walking fragments (routes), such as user movements between objects in a room, morning or other daytime walk out of the room and back, etc.
6. Parameters of a gait of a user may be initially determined for each walking fragment (route), such as walking from a door to a chair, from a table to a bed, walking out of a room, etc. Subsequently, the collected parameters may be processed and accumulated for each user routine; average gait speeds and other analytics and statistics for various routines may also be produced and stored; gait patterns may be identified.
7. Machine learning may be employed to build an automatic classifier or a set of automatic classifiers for various routines, taking key gait parameters from a new walking fragment and classifying the fragment either as corresponding to gait patterns or deviating from such patterns. Training data may include runtime gait parameters, analytics and statistics built according to user activities or a combination of user activities.

The system may continuously monitor a gait of a user for all routines, detecting and reporting abnormalities, such as significant speed deviations from statistical averages and ranges.

BRIEF DESCRIPTION OF THE DRAWINGS

Embodiments of the system described herein will now be explained in more detail in accordance with the figures of the drawings, which are briefly described as follows.

FIGS. 3A-3B are schematic illustrations of building statistics of gait parameters for user routines, according to an embodiment of the system described herein.

DETAILED DESCRIPTION OF VARIOUS EMBODIMENTS

The system described herein provides a mechanism for continuous non-contact identification of walking direction and gait speed, accumulating gait statistics and patterns associated with everyday user routines, detecting and reporting gait abnormalities based on data represented by point clouds, captured by an always-on tracking device, embedded into a room or other facility where the user resides.

Figure 1:
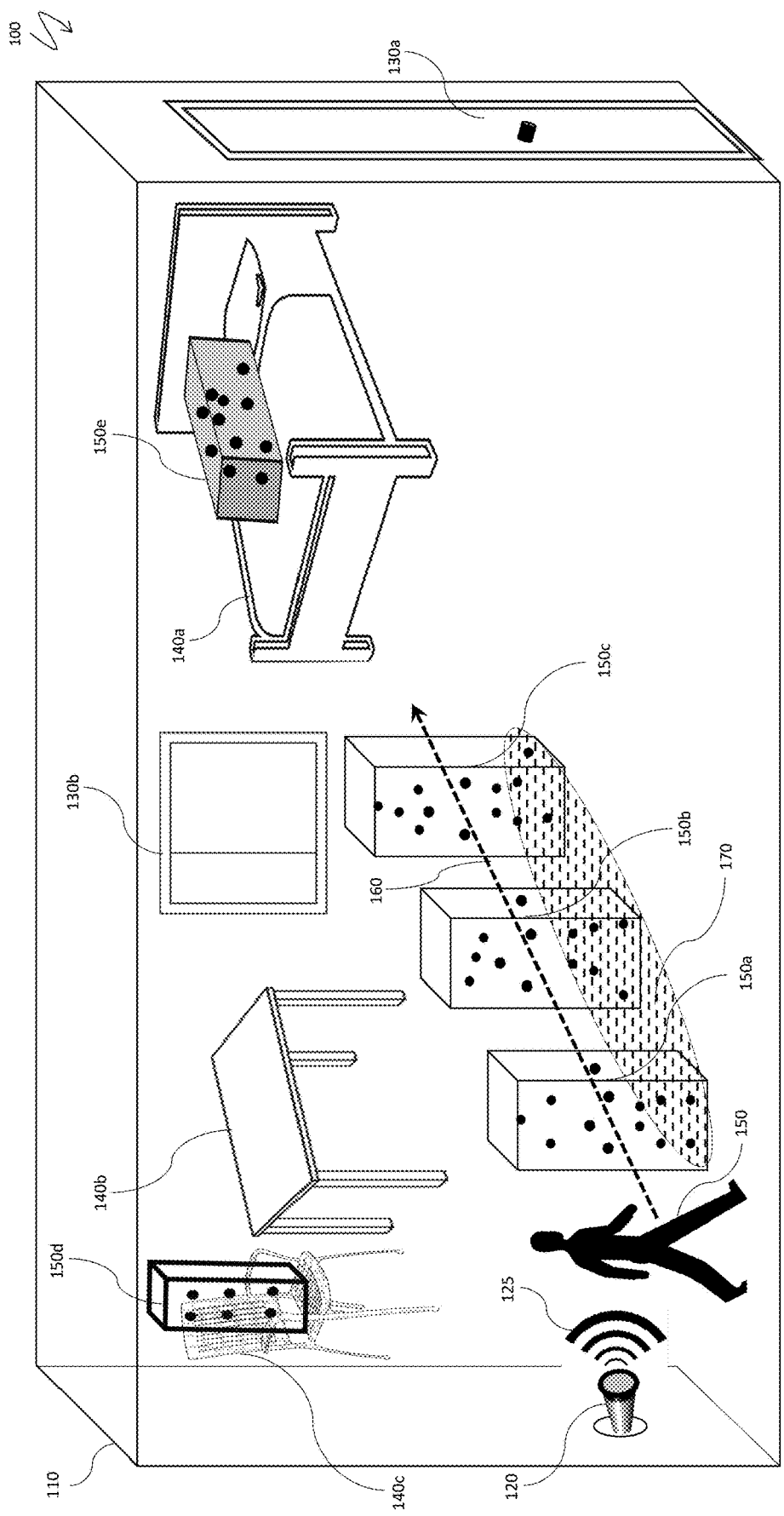
FIG. 1 is a schematic illustration of a furnished room with a non-contact tracking device and point clouds for different user states, according to an embodiment of the system described herein.

FIG. 1 is a schematic illustration 100 of a furnished room with a non-contact tracking device and point clouds for different user states. A room 110 with a non-contact tracking device 120 emitting a radar signal 125 has a door 130a, a window 130b and is furnished with a bed 140a, a table 140b and a chair 140c. A user 150 walks across the room and movement of the user 150 is captured through a sequence of point clouds 150a, 150b, 150c captured by the tracking device 120 at adjacent time frames. Two important characteristics of movement of the user 150 are a walking direction 160 and a walking band 170. Two other point clouds 150d, 150e with lower point density (compared to the point clouds 150a, 150b, 150c associated with walking), represent a sitting state and a lying down state, respectively, of the user 150.

Figure 2B:
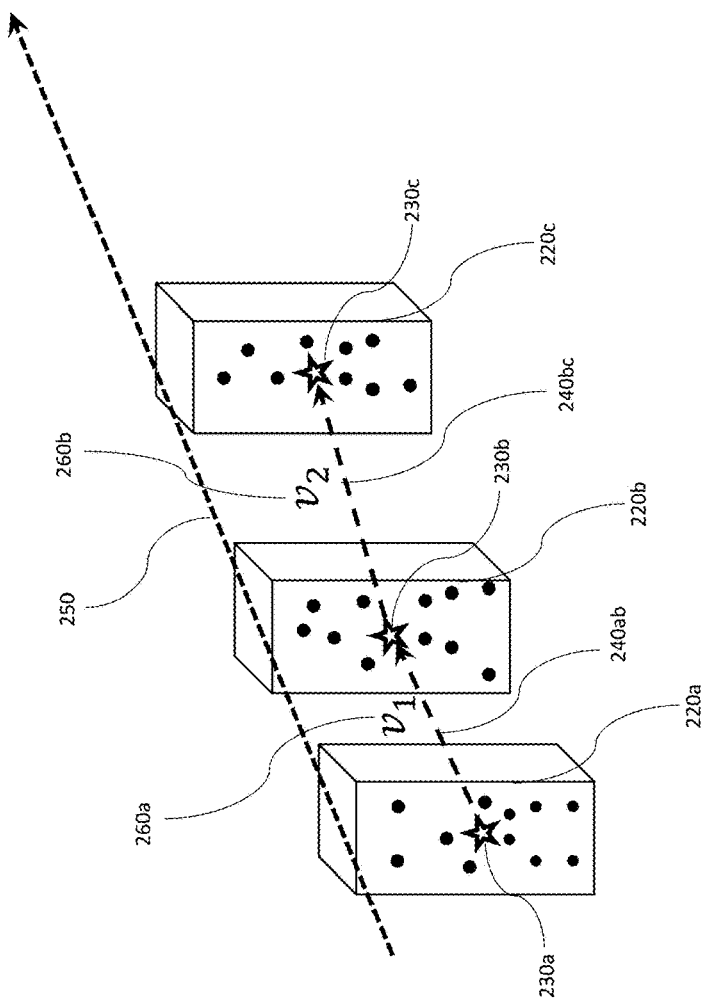
FIGS. 2A-2B are schematic illustrations of the cleaning up of point clouds and identifying a walking direction, momentary velocities, speed and gait band according to an embodiment of the system described herein.
Figure 2A:
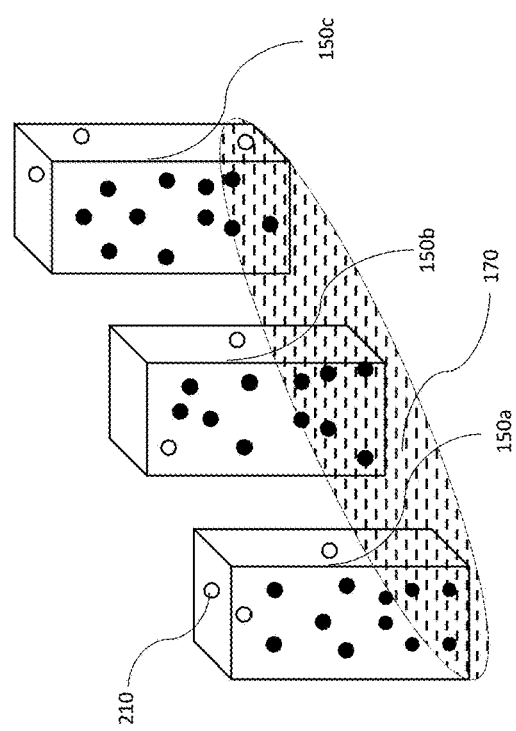

FIGS. 2A-2B are schematic illustrations of cleaning up of point clouds and identifying a walking direction, momentary velocities and speed. The point clouds 150a, 150b, 150c in FIG. 2A, showing user positions at three consecutive frames (see FIG. 1 for details) and the corresponding walking band 170, are pre-processed; unreliable data points 210 resulting, for example, from device or environment noise, are filtered out to form more representative and compact data samples. FIG. 2B shows the cleaned-up point clouds 220a, 220b, 220c. Positions of centroids 230a, 230b, 230c for the cleaned-up point clouds 220a, 220b, 220c are calculated, and momentary walking directions, represented by vectors 240ab, 240bc, connecting adjacent ones of the centroids 230a, 230b, 230c, are identified. Momentary walking directions are used to approximate a general walking direction 250, for example, as a straight line minimizing the square error deviation from the set of momentary walking directions. The momentary walking directions also provide estimates of momentary walking velocities $260a$ ($v_1$) and $260b$ ($v_2$), which, in turn, define the momentary walking speeds according to a formula: $S_i=|v_i|$. The walking speed in the general walking direction may be calculated based on the distance along the general walking direction through a sequence of frames and the time difference between the last and the first frame in the sequence.

FIGS. 3A-3B are schematic illustrations of building statistics of gait parameters for user routines. FIG. 3A shows a plan of the furnished room 110 from FIG. 1 (non-contact tracking device and emitted radio wave are not shown in FIG. 3), with the door 130a, the window 130b and the furniture items, the bed 140a, the table 140b, and the chair 140c. A user 310 walks over a total of four routes at different times, as follows:

1. A route 330a, corresponds to entering the room through the door 130a and walking to the chair 140c (denoted by a walking state 340a) where the user 310 stands (denoted by a standing state 340b) and then sits for a while (denoted by a sitting state 340c). A walking band 320 is shown at a mid-position of the route 330a for an illustration purpose.
2. A route 330b corresponds to walking from the char 140c to the window 130b, where the user briefly stands.
3. A route 330c corresponds to the user 310 walking from the window 130b to the bed 140a where the user 310 lays down (denoted by a state 340d) and stays for a while.
4. Subsequently, the user 310 sits on the bed 140a, stands up and walks along a route 330d to leave the room 110 (denoted by a departed state 340e).

The system captures and processes walking directions and speeds for the user 310 for all four routes 330a-330d. Average user speeds for all the routes 330a-330d are shown as items 270a-270d ($\bar{S}_1$-$\bar{S}_4$).

Sequences of user states (walking, standing, sitting, laying down, departing from the room) may be categorized and grouped to form a set of user routines 350 ($R_1$-$R_4$). Statistics of average gate speed ranges 360 are shown on a graph 370 of FIG. 3B and represent gait patterns of the user 310 of FIG. 3A.

Figure 4:
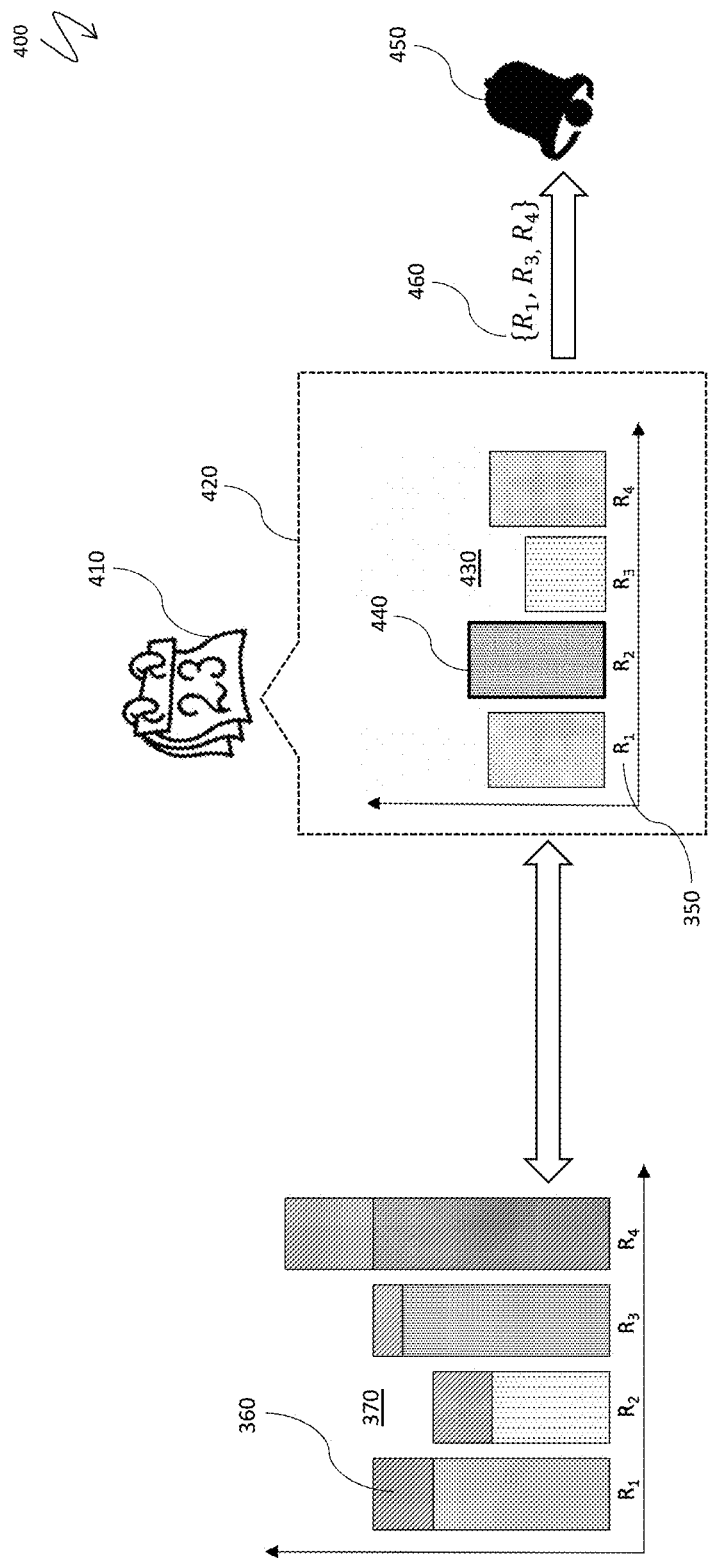
FIG. 4 is a schematic illustration of monitoring newly captured gait data, detecting, and notifying about gait abnormalities, according to an embodiment of the system described herein.

FIG. 4 is a schematic illustration 400 of monitoring newly captured gait data and detecting and notifying about gait abnormalities. The graph 370 shows an established distribution of walking speed ranges that represents user walking (gait) patterns for various daily routines (sets of activities and the corresponding states and state transitions, as explained in more details in conjunction with FIG. 3). A continuous non-contact monitoring of user activities at various calendar dates 410 may provide the system with a one-time set of field data 420 and enable building a distribution of average gait speeds 430 for the known set of the user routines 350. If the distribution 430 shows a significant deviation from the gait patterns, that is, from average gait speeds for some or all of the routines 350 from the established ranges 360, it may signal some problems with user gait, potentially translating into medical emergencies. FIG. 4 illustrates a situation when gait speed averages calculated for field data seriously deviate from the established ranges 360 for three out of four routines; only a routine 440 has an average speed value that belongs to an anticipated range. In this situation, the system may generate a list of routines with potentially abnormal user behavior and send an alarm 450 to care personnel, and may supplement the alarm with a list 460 of affected user routines.

Figure 5:
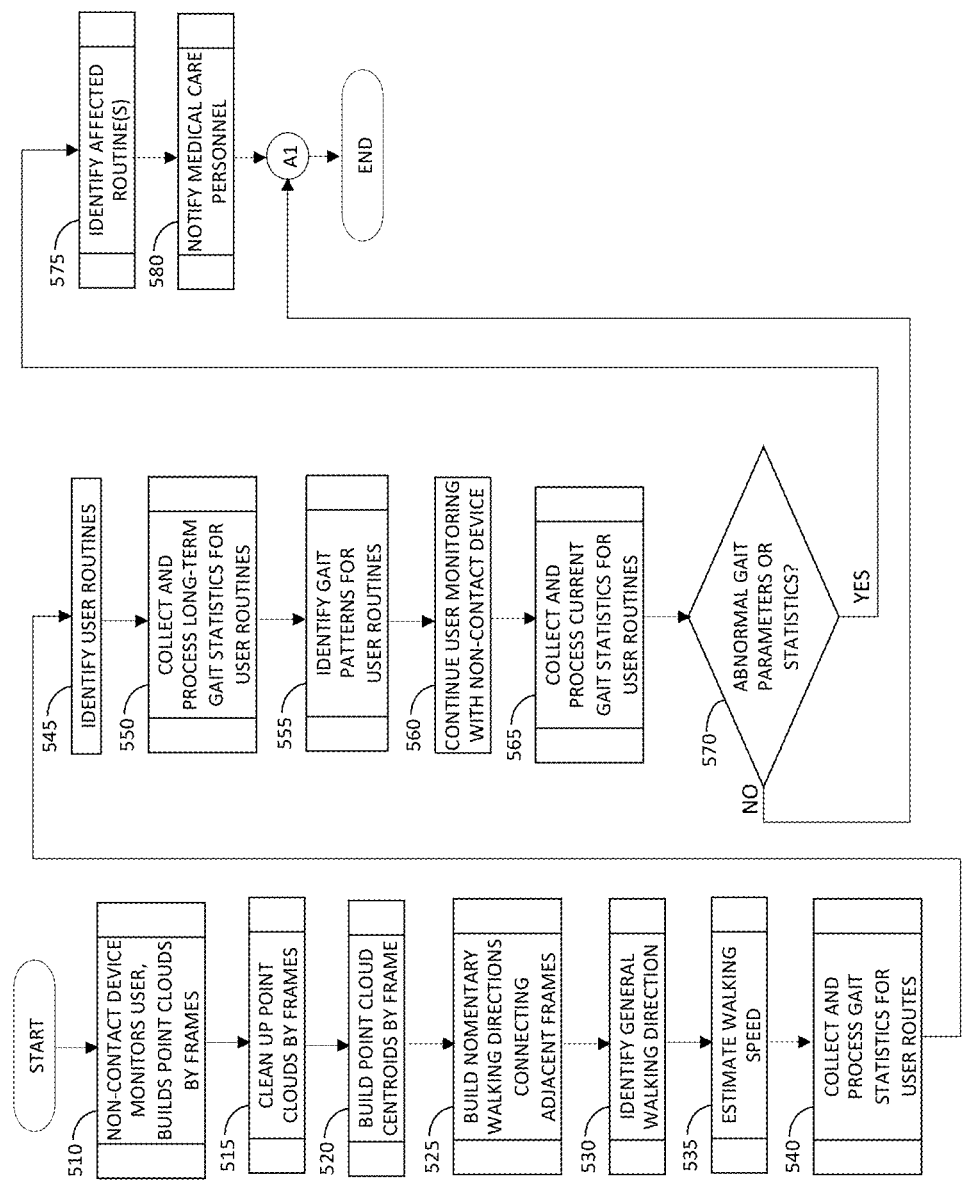
FIG. 5 is a system flow diagram illustrating system functioning in connection with identifying gait parameters and patterns and reporting gait abnormalities, according to an embodiment of the system described herein.

Referring to FIG. 5, a system flow diagram 500 illustrates system functioning in connection with identifying gait parameters and patterns and reporting gait abnormalities. Processing begins at a step 510, where a non-contact device monitors a user and builds point clouds that are made available to the system at subsequent polling frames. After the step 510, processing proceeds to a step 515, where the point clouds are cleaned up by frames, as explained elsewhere herein (see, for example, FIGS. 2A-2B and the accompanying text). After the step 515, processing proceeds to a step 520, where the system builds centroids for the point clouds (see items 230a, 230b, 230c in FIG. 2B). After the step 520, processing proceeds to a step 525, where the system builds vectors of momentary of walking directions connecting adjacent frames (see items 240*ab*, 240*bc* in FIG. 2B). After the step 525, processing proceeds to a step 530, where the system identifies a general walking direction (for example, by solving an optimization task based on momentary walking directions, as explained elsewhere herein). After the step 530, processing proceeds to a step 535, where the system estimates the walking speed (see FIG. 2B and the accompanying text).

After the step 535, processing proceeds to a step 540, where the system collects and processes gait statistics for user routes, as explained in conjunction with FIGS. 3A-3B. After the step 540, processing proceeds to a step 545, where the system identifies user routines by grouping sequences of user states and state transitions. After the step 545, processing proceeds to a step 550, where the system collects and processes gait patterns, i.e. the long-term gait statistics for walking fragments of user routines (see, for example, graph 370 in FIGS. 3B, 4). After the step 550, processing proceeds to a step 555, where gait patterns for user routines are identified. After the step 555, processing proceeds to a step 560, where the system continues user monitoring with a non-contact tracking device. After the step 560, processing proceeds to a step 565, where the system collects and processes current (field) gait statistics for previously established user routines. After the step 565, processing proceeds to a test step 570, where it is determined whether abnormal gait parameters or statistics in the current gait data have been observed, explained in FIG. 4 and the accompanying text. If not, processing is complete; otherwise, processing proceeds to a step 575, where the system identifies affected routine(s). After the step 575, processing proceeds to a step 580, where medical care personnel are notified. After the step 580, processing is complete.

Various embodiments discussed herein may be combined with each other in appropriate combinations in connection with the system described herein. Additionally, in some instances, the order of steps in the flowcharts, flow diagrams and/or described flow processing may be modified, where appropriate. Subsequently, system configurations and functions may vary from the illustrations presented herein. Further, various aspects of the system described herein may be implemented using various applications and may be deployed on various devices, including, but not limited to smartphones, tablets and other mobile computers. Smartphones and tablets may use operating system(s) selected from the group consisting of: iOS, Android OS, Windows Phone OS, Blackberry OS and mobile versions of Linux OS. Mobile computers and tablets may use operating system selected from the group consisting of Mac OS, Windows OS, Linux OS, Chrome OS.

Software implementations of the system described herein may include executable code that is stored in a computer readable medium and executed by one or more processors. The computer readable medium may be non-transitory and include a computer hard drive, ROM, RAM, flash memory, portable computer storage media such as a CD-ROM, a DVD-ROM, a flash drive, an SD card and/or other drive with, for example, a universal serial bus (USB) interface, and/or any other appropriate tangible or non-transitory computer readable medium or computer memory on which executable code may be stored and executed by a processor. The software may be bundled (pre-loaded), installed from an app store or downloaded from a location of a network operator. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A method of determining gait patterns and abnormalities of a user, comprising:
    forming a plurality of point clouds corresponding to the user, each of the point clouds being three-dimensional coordinates of moving points, frame by frame, through a data capturing session;
    determining centroids of the point clouds;
    determining momentary walking velocities using estimates based on vectors connecting the centroids for adjacent frames captured during walking of the user;
    determining gait speed for the user based on the momentary walking velocities;
    determining at least one distribution of gait speeds for the user; and
    detecting gait abnormalities based on deviation of the gait speed from the at least one distribution of gait speeds.

2. The method, according to claim 1, wherein detecting a plurality of point clouds includes using a tracking device to capture movements of the user.

3. The method, according to claim 2, wherein the tracking device uses at least one of: radar or lidar.

4. The method, according to claim 2, wherein the movements are associated with states corresponding to at least one of: walking, standing, sitting, lying down on a bed, lying down on a floor, and departing a room.

5. The method, according to claim 2, further comprising: determining a gait pattern of the user corresponding to routines of the user based on routes walked by the user, wherein a separate one of the at least one distribution of gait speeds is provided for each of the routines.

6. The method, according to claim 5, further comprising: providing an alarm in response to detecting gait speeds for a subset of the routines that deviate from the gait pattern.

7. The method, according to claim 6, wherein the alarm is provided with identification of specific ones of the routines for which the gait speed of the user deviates.

8. The method, according to claim 5, wherein the routes correspond to the movements of the user between objects in a room.

9. A non-transitory computer readable medium containing software that determines gait patterns and abnormalities of a user, the software comprising:
    executable code that forms a plurality of point clouds corresponding to the user, each of the point clouds being three-dimensional coordinates of moving points, frame by frame, through a data capturing session;
    executable code that determines centroids of the point clouds;
    executable code that determines momentary walking velocities using estimates based on vectors connecting the centroids for adjacent frames captured during walking of the user;
    executable code that determines gait speed for the user based on the momentary walking velocities;
    executable code that determines at least one distribution of gait speeds for the user; and
    executable code that detects gait abnormalities based on deviation of the gait speed from the at least one distribution of gait speeds.

10. The non-transitory computer readable medium, according to claim 9, wherein detecting a plurality of point clouds includes using a tracking device to capture movements of the user.

11. The non-transitory computer readable medium, according to claim 10, wherein the tracking device uses at least one of: radar or lidar.

12. The non-transitory computer readable medium, according to claim 10, wherein the movements are associated with states corresponding to at least one of: walking, standing, sitting, lying down on a bed, lying down on a floor, and departing a room.

13. The non-transitory computer readable medium, according to claim 10, further comprising: executable code that determines a gait pattern of the user corresponding to routines of the user based on routes walked by the user, wherein a separate one of the at least one distribution of gait speeds is provided for each of the routines.

14. The non-transitory computer readable medium, according to claim 13, further comprising: executable code that provides an alarm in response to detecting gait speeds for a subset of the routines that deviate from the gait pattern.

15. The non-transitory computer readable medium, according to claim 14, wherein the alarm is provided with identification of specific ones of the routines for which the gait speed of the user deviates.

16. The non-transitory computer readable medium, according to claim 13, wherein the routes correspond to the movements of the user between objects in a room.

* * * * *